(12) United States Patent
Moshe et al.

(10) Patent No.: US 8,953,158 B2
(45) Date of Patent: Feb. 10, 2015

(54) GRADING OF AGRICULTURAL PRODUCTS VIA HYPER SPECTRAL IMAGING AND ANALYSIS

(76) Inventors: Danny S. Moshe, Kiryat Ono (IL); Henry M. Dante, Midlothian, VA (US); Seetharama C. Deevi, Midlothian, VA (US); Curtis M. Hinton, Glen Allen, VA (US)

( * ) Notice: Subject to any disclaimer, the term of this patent is extended or adjusted under 35 U.S.C. 154(b) by 401 days.

(21) Appl. No.: 13/394,187

(22) PCT Filed: Sep. 2, 2010

(86) PCT No.: PCT/IB2010/053952
§ 371 (c)(1),
(2), (4) Date: Jun. 19, 2012

(87) PCT Pub. No.: WO2011/027315
PCT Pub. Date: Mar. 10, 2011

(65) Prior Publication Data
US 2012/0250025 A1    Oct. 4, 2012

Related U.S. Application Data

(60) Provisional application No. 61/239,799, filed on Sep. 4, 2009.

(51) Int. Cl.
*G01J 3/00* (2006.01)
*B07C 5/342* (2006.01)
(Continued)

(52) U.S. Cl.
CPC ............... *B07C 5/3422* (2013.01); *G01N 21/85* (2013.01); *G01N 2021/845* (2013.01); *G01N 2021/8466* (2013.01)
USPC .......................................... 356/300; 356/451

(58) Field of Classification Search
CPC ................. B07C 5/3422; G01N 21/85; G01N 2012/8466; G01N 2021/845; G01N 21/658; G01J 3/45; G01J 3/30; G01J 3/02; G06F 17/30
USPC .......... 209/576–582, 585, 587; 356/300–334; 250/339.07, 339.12, 910; 435/288.7
See application file for complete search history.

(56) References Cited

U.S. PATENT DOCUMENTS

| 4,778,987 A | 10/1988 | Saaski et al. |
| 5,085,325 A | 2/1992 | Jones et al. |

(Continued)

FOREIGN PATENT DOCUMENTS

WO    WO 00/58035    10/2000

OTHER PUBLICATIONS

International Preliminary Report on Patentability Dated Mar. 15, 2012 From the International Bureau of WIPO Re. Application No. PCT/IB2010/053952.

(Continued)

*Primary Examiner* — Tarifur Chowdhury
*Assistant Examiner* — Michael P Lapage

(57) ABSTRACT

A system for grading an agricultural product employing hyper-spectral imaging and analysis. The system includes at least one light source for providing a beam of light, an interferometer or a prism array for dispersing electromagnetic radiation emitted from said agricultural product into a corresponding spectral image, a light measuring device for detecting component wavelengths within the corresponding spectral image and a processor operable to compare the detected component wavelengths to a database of previously graded agricultural products to identify and select a grade for the agricultural product. A method for grading an agricultural product via hyper-spectral imaging and analysis is also provided.

7 Claims, 9 Drawing Sheets

(51) Int. Cl.
*G01N 21/85* (2006.01)
*G01N 21/84* (2006.01)

(56) References Cited

U.S. PATENT DOCUMENTS

| | | | |
|---|---|---|---|
| 6,400,833 B1 * | 6/2002 | Richert | 382/110 |
| 6,646,264 B1 * | 11/2003 | Modiano et al. | 250/339.07 |
| 7,142,988 B1 * | 11/2006 | Johnson | 702/20 |
| 2002/0008055 A1 | 1/2002 | Campbell et al. | |
| 2005/0057263 A1 | 3/2005 | Moshe et al. | |

OTHER PUBLICATIONS

International Search Report and the Written Opinion Dated Dec. 22, 2010 From the International Searching Authority Re. Application No. PCT/IB2010/053952.

* cited by examiner

GRADING OF AGRICULTURAL PRODUCTS VIA HYPER SPECTRAL IMAGING AND ANALYSIS

RELATED APPLICATIONS

This application is a National Phase of PCT Patent Application No. PCT/IB2010/053952 having International filing date of Sep. 2, 2010, which claims the benefit of priority of U.S. Provisional Patent Application No. 61/239,799 filed on Sep. 4, 2009. The contents of the above applications are all incorporated herein by reference.

FIELD

Disclosed herein is a method and system for the grading of agricultural products, such as tobacco bales, using hyperspectral imaging and analysis.

ENVIRONMENT

Certain agricultural products, such as cultivated tobacco plants, are harvested for their leaves, which are then dried and cured. In the manufacture of cigarettes, blends of different types of tobaccos are frequently employed, with three main types of tobacco used in U.S. blends. These tobacco types are Virginia or flue-cured, Burley and Oriental.

Virginia, or flue-cured tobacco, is also called "bright tobacco" since it turns a bright yellow-orange color during curing. It grows particularly well in Georgia, Virginia and the Carolinas. Flue-curing is a heat driven process that reduces the risk of mold and promotes chemical changes that improve the sensory quality of the tobacco.

Burley tobacco is a slightly lighter green leaf than Virginia tobacco. It requires heavier soils and is grown in Maryland, Kentucky and elsewhere. After harvesting, Burley tobaccos are air cured to reduce the risk of mold and improve sensory quality. In contrast to flue-curing, air-curing takes place under ambient conditions.

Oriental tobacco is the smallest and hardiest of all tobacco types, grown principally in the Balkans, Turkey and the Middle East. These conditions and a high planting density create an aromatic flavor. Oriental tobacco is typically sun-cured.

These tobacco types may be further broken down into subgroups which may depend upon where the tobacco is grown, which part of the plant it is taken from, weather conditions and other characteristics that relate to the quality of the tobacco, including color, maturity, and uniformity. These sub-groupings are generally referred to as tobacco "grades."

One tobacco plant can produce several grades of leaf. The sensory, physical, chemical and visual properties of a tobacco grade are generally determined by the leaf position on the plant. For example, the leaves at the top of the plant have more exposure to the sun than the ones at the bottom and typically contain higher levels of nicotine and other alkaloids. The chemical content of the leaf can vary widely depending on the type of tobacco, the soil and environmental conditions where it was grown, the way it is cured and how it is matured.

Tobacco is packaged in the form of tobacco bales, graded and purchased from growers. A tobacco bale is a large, substantially rectangular shaped package of tobacco leaves and stems, tightly bound with a strong cord or wire or loosely packed in boxes. A typical Burley or Virginia tobacco bale may have dimensions on the order of at least about 1.2 meters per side and a corresponding volume on the order of at least about 1.7 cubic meters.

As for the case of any agricultural product, tobacco may be characterized by a wide variety of physical, chemical, and/or biological, (herein, also referred to as biophysicochemical) properties, characteristics, features, and behavior, which are associated with various aspects relating to agriculture, agronomy, horticulture, botany, environment, geography, climate, and ecology of the tobacco crop and plants thereof from which tobacco leaves are derived. Moreover, the biophysicochemical properties of tobacco leaves may be spatially (i.e., geographically) and temporally (i.e., seasonally) variable or dependent. Such definition and characterization of tobacco leaves are directly translatable and extendable to defining and characterizing tobacco bales.

In a general manner, testing of tobacco bales may be divided into two major aspects: a macro scale aspect, and a micro scale aspect, where these two major aspects relate to different types of properties, characteristics, features, and parameters of tobacco bales and of the tobacco leaves contained therein.

The first major aspect is associated with macro scale properties of tobacco bales, typically, generally with respect to whole individual tobacco bales, but not specifically with respect to single or individual tobacco leaves contained within the tobacco bales. Primary examples of macro scale testing include weight of individual tobacco bales; physical size dimensions of individual tobacco bales; packing density of individual tobacco bales; void volume of individual tobacco bales; and moisture (water) content or humidity of individual tobacco bales.

The second major aspect is associated with micro scale properties of tobacco bales, also generally with respect to individual tobacco bales, but specifically with respect to individual tobacco leaves contained within the tobacco bales, and more specifically with respect to a wide variety of numerous possible physical, chemical, and/or biological, (biophysicochemical) properties, characteristics, features, and parameters, of single or individual tobacco leaves contained within a given tobacco bale. Primary examples of such micro scale testing include physical shape and size dimensions of individual tobacco leaves; coloring of individual tobacco leaves; moisture (water) content of individual tobacco leaves; types, distribution, and composition of organic and inorganic chemical species or components of single or individual tobacco leaves; types, distribution, and composition of possible unknown or foreign (physical, chemical, and/or biological) matter or species (and biophysicochemical aspects thereof) on and/or within individual tobacco leaves; biophysicochemical behavior (activity and/or reactivity) of single or individual tobacco leaves in response to physical stimuli or effects, such as exposure to electromagnetic radiation; biophysicochemical behavior (activity and/or reactivity) of single or individual tobacco leaves in response to chemical stimuli or effects (such as exposure to aqueous liquids or to non-aqueous liquids; and biophysicochemical behavior (activity and/or reactivity) of individual tobacco leaves in response to biological stimuli or effects, such as exposure to biological organisms.

Ordinarily, it may be expected that the two major aspects or components of tobacco bale testing are essentially independent or separate from each other. However, depending upon (1) the particular macro scale and micro scale properties, characteristics, features, and parameters of the tobacco bales, and, depending upon (2) the particular (biophysicochemical) properties, characteristics, features, and behavior of individual tobacco leaves contained within the tobacco bales, and depending upon (3) the particular context of tobacco bale testing, then, one major aspect may influence another major aspect.

In general, grading of a tobacco bale involves systematically determining and assigning to that individual tobacco bale, a grade from among a number of grades listed in a known scale, series, or sequence of a range of such grades. Herein, the term grading means ranking, classifying, categorizing, grouping, arranging, and organizing. The term grade means rank, class, category, and group. Each grade is defined and characterized by a different measure of quality of tobacco bales, where the different measures of quality of the tobacco bales are measured and determined in accordance with the preceding described section of quality control testing of tobacco bales.

The forms disclosed herein are generally focused on the domains encompassing grading of tobacco bales, and are specifically focused on the domains encompassing automatic grading of tobacco bales that can be performed via hyper-spectral imaging and analysis.

In the general technique of spectral imaging, one or more objects in a scene or sample are affected in a way, such as excitation by incident electromagnetic radiation supplied by an external source of electromagnetic radiation upon the objects, which causes each object to emit electromagnetic radiation in the form of an emission beam featuring an emission spectrum.

Hyper-spectral imaging and analysis is a combined spectroscopy and imaging type of analytical method involving the sciences and technologies of spectroscopy and imaging. By definition, hyper-spectral imaging and analysis is based on a combination of spectroscopy and imaging theories, which are exploitable for analyzing samples of physical, chemical, and/or biological, (i.e., biophysicochemical) matter in a highly unique, specialized, and sophisticated, manner.

In hyper-spectral imaging, a field of view of a sample is scanned and imaged while the sample is exposed to electromagnetic radiation. During the hyper-spectral scanning and imaging there is generated and collected relatively large numbers of multiple spectral images, one-at-a-time, but, in an extremely fast sequential manner of the objects emitting electromagnetic radiation at a plurality of wavelengths and frequencies, where the wavelengths and frequencies are associated with different selected portions or bands of an entire hyper-spectrum emitted by the objects. A hyper-spectral imaging and analysis system can be operated in an extremely rapid manner for providing exceptionally highly resolved spectral and spatial data and information of an imaged sample of matter, with high accuracy and high precision, which are fundamentally unattainable by using standard spectral imaging and analysis.

In general, when electromagnetic radiation in the form of light, such as that used during hyper-spectral imaging, is incident upon an object, the electromagnetic radiation is affected by one or more of the physical, chemical, and/or biological species or components making up the object, by any combination of electromagnetic radiation absorption, diffusion, reflection, diffraction, scattering, and/or transmission, mechanisms. Moreover, an object whose composition includes organic chemical species or components, ordinarily exhibits some degree of fluorescent and/or phosphorescent properties, when illuminated by some type of electromagnetic radiation or light, such as ultra-violet (UV), visible (VIS), or infrared (IR), types of light. The affected electromagnetic radiation, in the form of diffused, reflected, diffracted, scattered, and/or transmitted, electromagnetic radiation emitted by the object is directly and uniquely related to the physical, chemical, and/or biological, (biophysicochemical) properties of the object, in general, and of the chemical species or components making up the object, in particular, and therefore represents a spectral fingerprint or signature pattern type of identification and characterization of the object.

A typical spectral imaging system consists of an automated measurement system and analysis software. The automated measurement system includes optics, mechanics, electronics, and peripheral hardware and software, for irradiating, typically using an illuminating source, a scene or sample, followed by measuring and collecting light emitted, for example, by fluorescence, from objects in the scene or sample, and for applying calibration techniques best suited for extracting desired results from the measurements. Analysis software includes software and mathematical algorithms for analyzing, displaying, and presenting, useful results about the objects in the scene or sample in a meaningful way.

The spectral intensity of each pixel in an optical image of a scene or sample is determined by collecting incident light emitted by objects in the scene or sample, passing the light through a prism array or an optical interferometer. An interferometer employs mirrors and outputs modulated light corresponding to a set of linear combinations of the spectral intensity of the light emitted from each pixel. Light exiting therefrom is focused onto a detector array or matrix, followed by independently and simultaneously scanning the optical path difference (OPD) generated for all pixels, and then processing the outputs of the detector array for determining the spectral intensity of each pixel needed for generating spectral (cube) images. In the case of interferometry, spectral imaging is practiced by utilizing various different types of interferometers wherein the OPD is varied, in order to synthesize the interferograms, by moving the entire interferometer, by moving an element within the interferometer, or by changing the angle of incidence of the incoming radiation. In each case, optical scanning of the interferometer enables synthesizing interferograms for all pixels of the imaged scene.

Each spectral image is a three dimensional data set of voxels (volume of pixels) in which two dimensions are spatial coordinates or position, (x, y), in an object and the third dimension is the wavelength, ($\lambda$), of the emitted light of the object, such that coordinates of each voxel in a spectral image may be represented as (x, y, $\lambda$). Any particular wavelength, ($\lambda$), of imaged light of the object is associated with a set of spectral images each featuring spectral fingerprints of the object in two dimensions, for example, along the x and y directions, whereby voxels having that value of wavelength constitute the pixels of a monochromatic image of the object at that wavelength. Each spectral image, featuring a range of wavelengths of imaged light of the object is analyzed to produce a two dimensional map of one or more physico-chemical properties, for example, geometrical shape, form, or configuration, and dimensions, and/or chemical composition, of the object and/or of components of the object, in a scene or sample.

In hyper-spectral imaging, multiple images of each object are generated from object emitted electromagnetic radiation having wavelengths and frequencies associated with different selected parts or bands of an entire spectrum emitted by the object. For example, hyper-spectral images of an object are generated from object emitted electromagnetic radiation having wavelengths and frequencies associated with one or more of the following bands of an entire spectrum emitted by the object: the visible band, spanning the wavelength range of about 400-700 nanometers, the infra-red band, spanning the wavelength range of about 800-1200 nanometers, and the deep infra-red band, spanning the wavelength range of about 3-12 microns. If proper wavelengths and wavelength ranges are used during hyper-spectral imaging, data and information of the hyper-spectral images are optimally used for detecting and analyzing by identifying, discriminating, classifying, and quantifying, the imaged objects and/or materials, for example, by analyzing different signature spectra present in pixels of the hyper-spectral images.

One example of a spectral imaging technique is a method and system for real-time, on-line chemical analysis of particulate samples, for example, polycyclic aromatic hydrocarbon (PAH) particles in aerosols, in which the PAH sample is excited to emit light, for example fluorescence, as disclosed in U.S. Pat. No. 5,880,830, the contents of which is incorporated by reference for all purposes as if fully set forth herein. In U.S. Pat. No. 5,880,830, spectral imaging techniques are used for acquiring images and analyzing properties of fixed position PAH particles in an aerosol. Air is sampled by means of a high volume pump sucking a large volume of air featuring aerosol contaminated with PAH particles onto a substrate, followed by on-line imaging and scene analysis of the stationary particles.

A method of calibration and real-time analysis of particles is described in U.S. Pat. No. 6,091,843, to Moshe et al., and is incorporated by reference for all purposes as if fully set forth herein. The method described, is based upon using essentially the same system of U.S. Pat. No. 5,880,830, for acquiring spectral images of static particles on a filter. Targets are identified in static particle images and are classified according to morphology type and spectrum type. Each target is assigned a value of an extensive property. A descriptor vector is formed, where each element of the descriptor vector is the sum of the extensive property values for one target class. The descriptor vector is transformed, for example, to a vector of mass concentrations of chemical species of interest, or of number concentrations of biological species of interest, using a relationship determined in the calibration procedure. In the calibration procedure, spectral images of calibration samples of static particles having known composition are acquired, and empirical morphology types and spectrum types are inferred from the spectral images. Targets are identified in the calibration spectral images, classified according to morphology type and spectrum type, and assigned values of an extensive property. For each calibration sample, a calibration descriptor vector and a calibration concentration vector is formed. A collective relationship between the calibration descriptor vectors and the calibration concentration vectors is found using chemometric methods.

A high speed hyper-spectral imaging system is often required for different types of repeatable and non-repeatable chemical and physical processes taking place during the sub-100 millisecond time scale, which cannot, therefore, be studied using regular hyper-spectral imaging techniques. Combustion reactions, impulse spectro-electrochemical experiments, and inelastic polymer deformations, are examples of such processes. Remote sensing of objects in distant scenes from rapidly moving platforms, for example, satellites and airplanes, is another example of a quickly changing observable that is often impossible to repeat, and therefore requires high speed hyper-spectral imaging.

Specific hardware for hyper-spectral imaging includes filter wheels and circular variable filters as disclosed in U.S. Pat. No. 5,591,981, U.S. Pat. No. 5,784,152, and U.S. Pat. No. 5,410,371; angle-tuned interference filters as in the Renishaw imaging Raman microscope described in U.S. Pat. No. 5,442,438; acousto-optical tunable filters (AOTFs) as disclosed in U.S. Pat. No. 5,216,484, U.S. Pat. No. 5,377,003, U.S. Pat. No. 5,556,790, and U.S. Pat. No. 5,379,065; and optical interferometers as disclosed in U.S. Pat. No. 5,835,214, U.S. Pat. No. 5,817,462, U.S. Pat. No. 5,539,517, and U.S. Pat. No. 5,784,162.

Hyper-spectral images generated by and collected from a sample of matter may be processed and analyzed by using automatic pattern recognition and/or optical character recognition types of hyper-spectral imaging data and information processing and analysis, for identifying, characterizing, and/or classifying, the physical, chemical, and/or biological, (biophysicochemical) properties of the hyper-spectrally imaged objects in the sample of matter.

While hyper-spectral analysis has been proposed for use with certain agricultural products, significant limitations exist with respect to such attempts. For example, problems that would preclude the applicability of past attempts include the relatively large size of typical tobacco bales and the fact that physical, chemical, and/or biological, (biophysicochemical) properties of tobacco leaves and, therefore, of tobacco bales, are spatially (i.e., geographically) and temporally (i.e., seasonally) variable or dependent. As such, despite the foregoing advances, there remains a need for a method and system for grading agricultural products, such as tobacco bales, via hyper-spectral imaging and analysis.

SUMMARY

Disclosed herein is a method and system for the grading of agricultural products, including tobacco bales, via hyper-spectral imaging and analysis. The method and system disclosed herein provide high sensitivity, high resolution, and high speed during operation, in a highly efficient, cost effective and commercially applicable manner.

In one aspect, disclosed herein is a system for grading an agricultural product employing hyper-spectral imaging and analysis. The system includes at least one light source for providing a beam of light of different wavelengths, an interferometer or prism array for dispersing electromagnetic radiation emitted from the beam of light into a corresponding spectral image, a light measuring device for detecting component wavelengths within the corresponding spectral image and a processor operable to compare the detected component wavelengths to a database of previously graded agricultural products to identify and select a grade for the agricultural product.

In another aspect, provided is a method for grading of an agricultural product via hyper-spectral imaging and analysis. The method includes the steps of scanning a plurality of regions of interest along the agricultural product, generating hyper-spectral images from the scanned regions of interest, forming a spectral fingerprint for the agricultural product from the hyper-spectral images, comparing the spectral fingerprint data to tobacco grade pattern data of previously graded agricultural product and determining a product grade for the agricultural product.

In yet another aspect, disclosed herein is a system for facilitating the purchase of a tobacco bale. The system includes an automatic on-line grading system employing hyper-spectral imaging and analysis and means for automatically determining bale weight and moisture content for the tobacco bale.

In still yet another aspect, disclosed herein is a method of facilitating tobacco purchasing. The method includes the steps of determining bale weight for a tobacco bale, determining moisture content for the tobacco bale and determining tobacco grade via hyper-spectral imaging and analysis. In one form, the step of determining tobacco grade via hyper-spectral imaging and analysis includes the steps of scanning a plurality of regions of interest along the tobacco bale, generating hyper-spectral images from the scanned regions of interest, forming a spectral fingerprint for the agricultural product from the hyper-spectral images, determining a physicochemical code for the tobacco bale and comparing the spectral fingerprint and physicochemical code data to tobacco grade pattern data of previously graded tobacco bales and determining a product grade for the tobacco bale.

In a further aspect, an apparatus for providing multiple fields of view from a single scan zone to a system for grading agricultural products employing hyper-spectral imaging and analysis is provided. The apparatus includes at least one light source for providing a beam of light and means for splitting the beam of light from the at least one light source into a plurality of light beams, to provide multiple fields of view to the hyper-spectral imaging and analysis system.

Certain forms disclosed herein are focused on the domain encompassing the testing of agricultural products, including tobacco bales, based on measuring, analyzing, and determining micro scale properties, characteristics, features, and parameters, generally with respect to individual bales, and specifically with respect to individual leaves contained within the bales. A wide variety of physical, chemical, and/or biological, (biophysicochemical) properties may be determined. Grading of agricultural products, including tobacco bales, is provided. Certain forms disclosed herein may be performed in an automatic on-line manner, via hyper-spectral imaging and analysis.

Certain forms disclosed herein include definition and use of the hyper-spectrally detectable and classifiable biophysicochemical (BPC) codes. In turn, the classified at least part of the single or individual tobacco contained within that particular tobacco bale is usable as part of a procedure for grading that particular tobacco bale.

Certain forms disclosed herein provide for tracking and accounting for the spatial (i.e., geographical) and temporal (i.e., seasonal) variability of physical, chemical, and/or biological, (biophysicochemical) properties and behavior of tobacco leaves and therefore, of tobacco bales. Such spatial and temporal variability or dependency of tobacco leaves, and therefore, of tobacco bales, can be uniquely tracked and accounted for by use of the hyper-spectrally detectable and classifiable biophysicochemical (BPC) codes and can therefore be incorporated into a procedure for grading tobacco bales.

Certain forms disclosed herein are implemented according to a temporal gated type of hyper-spectral imaging and analysis. Accordingly, in some forms thereof, a method and system for the grading of tobacco bales via temporal gated hyper-spectral imaging and analysis.

Certain forms disclosed herein are implemented by performing steps or procedures, and sub-steps or sub-procedures, in a manner selected from the group consisting of manually, semi-automatically, fully automatically, and combinations thereof, involving use and operation of system units, system sub-units, devices, assemblies, sub-assemblies, mechanisms, structures, components, and elements, and, peripheral equipment, utilities, accessories, and materials. Moreover, according to actual steps or procedures, sub-steps or sub-procedures, system units, system sub-units, devices, assemblies, sub-assemblies, mechanisms, structures, components, and elements, and, peripheral equipment, utilities, accessories, and materials, used for implementing a particular form, the steps or procedures, and sub-steps or sub-procedures are performed by using hardware, software, and/or an integrated combination thereof, and the system units, sub-units, devices, assemblies, sub-assemblies, mechanisms, structures, components, and elements, and peripheral equipment, utilities, accessories, and materials, operate by using hardware, software, and/or an integrated combination thereof.

For example, software used, via an operating system, for implementing certain forms disclosed herein can include operatively interfaced, integrated, connected, and/or functioning written and/or printed data, in the form of software programs, software routines, software sub-routines, software symbolic languages, software code, software instructions or protocols, software algorithms, or a combination thereof. For example, hardware used for implementing certain forms disclosed herein can include operatively interfaced, integrated, connected, and/or functioning electrical, electronic and/or electromechanical system units, sub-units, devices, assemblies, sub-assemblies, mechanisms, structures, components, and elements, and, peripheral equipment, utilities, accessories, and materials, which may include one or more computer chips, integrated circuits, electronic circuits, electronic sub-circuits, hard-wired electrical circuits, or a combination thereof, involving digital and/or analog operations. Certain forms disclosed herein can be implemented by using an integrated combination of the just described exemplary software and hardware.

In certain forms disclosed herein, steps or procedures, and sub-steps or sub-procedures can be performed by a data processor, such as a computing platform, for executing a plurality of instructions. Optionally, the data processor includes volatile memory for storing instructions and/or data, and/or includes non-volatile storage, for example, a magnetic hard-disk and/or removable media, for storing instructions and/or data. Optionally, certain forms disclosed herein include a network connection. Optionally, certain forms disclosed herein include a display device and a user input device, such as a keyboard and/or mouse.

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Figure 1:
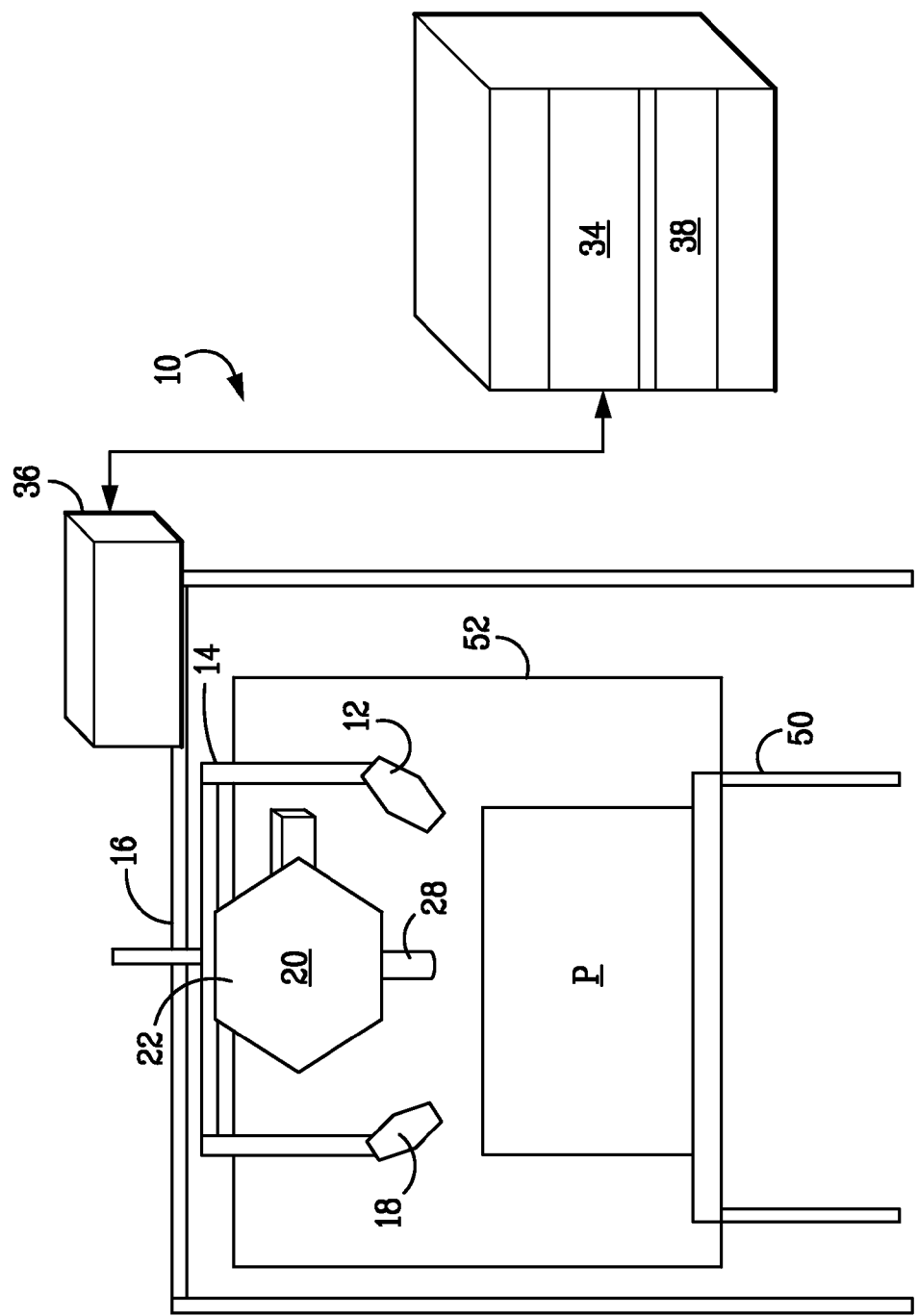
FIG. 1 presents, in schematic form, a system for grading an agricultural product employing hyper-spectral imaging and analysis, in accordance herewith.

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-9, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range from 1 to 6 also refers to, and encompasses, all possible sub-ranges, such as from 1 to 3, from 1 to 4, from 1 to 5, from 2 to 4, from 2 to 6, from 3 to 6, etc., and individual numerical values, such as 1, 1.3, 2, 2.8, 3, 3.5, 4, 4.6, 5, 5.2, and 6, within the stated or described numerical range of from 1 to 6. This applies regardless of the numerical breadth, extent, or size, of the stated or described numerical range.

Moreover, for stating or describing a numerical range, the phrase "in a range of between about a first numerical value and about a second numerical value," is considered equivalent to, and meaning the same as, the phrase "in a range of from about a first numerical value to about a second numerical value," and, thus, the two equivalently meaning phrases may be used interchangeably. For example, for stating or describing the numerical range of room temperature, the phrase "room temperature refers to a temperature in a range of between about 20° C. and about 25° C.," is considered equivalent to, and meaning the same as, the phrase "room temperature refers to a temperature in a range of from about 20° C. to about 25° C."

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Moreover, all technical and scientific words, terms, and/or phrases, introduced, defined, described, and/or exemplified, in the above sections, are equally or similarly applicable in the illustrative description, examples and appended claims.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, and materials, as well as operation and implementation, of exemplary forms, alternative forms, specific configurations, and, additional and optional aspects, characteristics, or features, thereof, of the methods, and of the systems, disclosed herein, are better understood with reference to the following illustrative description and accompanying drawings. Throughout the following illustrative description and accompanying drawings, same reference notation and terminology (i.e., numbers, letters, and/or symbols), refer to same system units, system sub-units, devices, assemblies, sub-assemblies, mechanisms, structures, components, elements, and configurations, and, peripheral equipment, utilities, accessories, and materials, components, elements, and/or parameters.

Disclosed herein, is a method, and system, for the grading of agricultural products, such as tobacco bales, via hyperspectral imaging and analysis. In certain forms thereof, provided are methodologies, protocols, procedures and equipment that are highly accurate and highly precise, in that they are reproducible and robust, when evaluating agricultural products, such as tobacco bales. The testing methodologies disclosed herein exhibit high sensitivity, high resolution, and high speed during automatic on-line operation.

Certain forms disclosed herein are specifically focused on the domain encompassing measuring, analyzing, and determining, micro scale properties, characteristics, features, and parameters of agricultural products, such as tobacco bales, generally with respect to individual tobacco bales, and specifically with respect to single or individual tobacco leaves contained within the tobacco bales, and more specifically with respect to a wide variety of numerous possible physical, chemical, and/or biological, (biophysicochemical) properties, characteristics, features, and parameters of single or individual tobacco leaves contained within a given tobacco bale. In one form, provided is an automatic on-line grading system employing hyper-spectral imaging and analysis.

Certain forms disclosed herein use what will be referred to as "hyper-spectrally detectable and classifiable biophysicochemical (BPC) codes." As used herein, a "hyper-spectrally detectable and classifiable biophysicochemical code" is a micro scale property, characteristic, feature, or parameter of a particular bulk agricultural product, such as a tobacco bale, which is hyper-spectrally detectable by hyper-spectral imaging and analysis in a manner that the resulting hyper-spectral data and information, for example, hyper-spectral "fingerprint" or "signature" patterns are usable for classifying at least part of a single or individual tobacco leaf contained within that particular tobacco bale. In turn, the classified part of the single or individual tobacco leaf contained within that particular tobacco bale is usable as part of a procedure for grading that particular tobacco bale.

Accordingly, a "hyper-spectrally detectable and classifiable biophysicochemical (BPC) code" is defined, generally with respect to a particular individual agricultural product, such as a tobacco bale, and specifically with respect to a single or individual tobacco leaf contained within the particular tobacco bale, and more specifically with respect to a physical, chemical, and/or biological, (biophysicochemical) property, characteristic, feature, or parameter, of that single or individual tobacco leaf contained within that particular tobacco bale. The hyper-spectrally detectable and classifiable biophysicochemical (BPC) codes are usable as part of a procedure for (uniquely and unambiguously) grading tobacco bales.

Primary examples of micro scale testing for generating hyper-spectrally detectable and classifiable biophysicochemical (BPC) codes, include: physical (geometrical/morphological) shape or form and size dimensions of single or individual tobacco leaves; coloring of single or individual tobacco leaves; moisture (water) content of, or within, single or individual tobacco leaves; type, distribution, and compositional make-up, of (organic and inorganic) chemical species or components, of single or individual tobacco leaves; types, distribution, and compositional make-up, of possible unknown or foreign (physical, chemical, and/or biological) matter or species and biophysicochemical aspects thereof on, and/or within, single or individual tobacco leaves; biophysicochemical behavior (activity and/or reactivity) of single or individual tobacco leaves in response to physical stimuli or effects, such as exposure to electromagnetic radiation; biophysicochemical behavior (activity and/or reactivity) of single or individual tobacco leaves in response to chemical stimuli or effects, such as exposure to aqueous liquids or to non-aqueous (organic based) liquids; and biophysicochemical behavior (activity and/or reactivity) of single or individual tobacco leaves in response to biological stimuli or effects, such as exposure to biological organisms; physical (geometrical/morphological) shape or form and size dimensions of single or individual tobacco leaves; coloring of single or individual tobacco leaves; moisture content of, or within, single or individual tobacco leaves; types, distribution, and compositional make-up, of (organic and inorganic) chemical species or components, of single or individual tobacco leaves; types, distribution and compositional make-up of possible unknown or foreign (physical, chemical, and/or biological) matter or species and biophysicochemical aspects thereof on, and/or within, single or individual tobacco leaves; biophysicochemical behavior (activity and/or reactivity) of single or individual tobacco leaves in response to physical stimuli or effects, such as exposure to electromagnetic radiation; biophysicochemical behavior (activity and/or reactivity) of single or individual tobacco leaves in response to chemical stimuli or effects (such as exposure to aqueous (water based) liquids or to non-aqueous (organic based) liquids); and biophysicochemical behavior (activity and/or reactivity) of single or individual tobacco leaves in response to biological stimuli or effects, such as exposure to biological organisms.

In one form, tracking and accounting for the spatial (i.e., geographical) and temporal (i.e., seasonal) variability or dependency of physical, chemical, and/or biological, (biophysicochemical) properties, characteristics, features, and behavior, of agricultural products, such as tobacco bales and tobacco leaves are provided. Such spatial and temporal variability or dependency of tobacco leaves, and therefore, of tobacco bales, can be uniquely and unambiguously tracked and accounted for by use of the hyper-spectrally detectable and classifiable biophysicochemical (BPC) codes' and can therefore be incorporated into a procedure for (uniquely and unambiguously) grading tobacco bales.

In another form, temporal gated hyper-spectral imaging and analysis may be employed. Temporal gated hyper-spectral imaging and analysis is disclosed in WO 1999/53298, published on Oct. 21, 1999, the contents of which are hereby incorporated by reference in their entirety. As such, disclosed herein is a method and system for the automatic on-line grading of tobacco bales via temporal gated hyper-spectral imaging and analysis.

Referring now to FIG. 1, a system 10 for grading an agricultural product P employing hyper-spectral imaging and analysis is shown in schematic form. The system 10 includes at least one light source 12 for providing a beam of light. As shown, the at least one light source 12 may be mounted on an arm 14 for positioning at least one light source 12 in proximity to the agricultural product P positioned on platform 50. In one form, arm 14 is mounted to frame 16 and may be either fixed thereto or moveably positionable, as will be described hereinbelow. As shown in FIG. 1, a second light source 18 may also be provided and mounted to arm 14.

In one form, the at least one light source 12 for providing a beam of light of different wavelengths comprises a xenon light source. In another form, the at least one light source 12 for providing a beam of light comprises a mercury light source. In yet another form, the at least one light source or the second light source 18 comprises an ultraviolet light source for use in providing a chemical signature of the agricultural product P. This optional ultraviolet light source adds an additional media of classification that provides a better understanding of an agricultural product's quality. In still yet another form, the at least one light source 12 comprises a xenon light source, the second light source 18 comprises a mercury light source and a third light source (not shown) comprises an ultraviolet light source.

In one form, the at least one light source 12 and/or the second light source 18 may be positioned to minimize the angle of incidence of a beam of light with the agricultural product P.

As shown in FIG. 1, in order to segregate ambient light from the light provided by system 10, an enclosure 52 may be employed to provide a dark-room-like environment for system 10.

Figure 2:
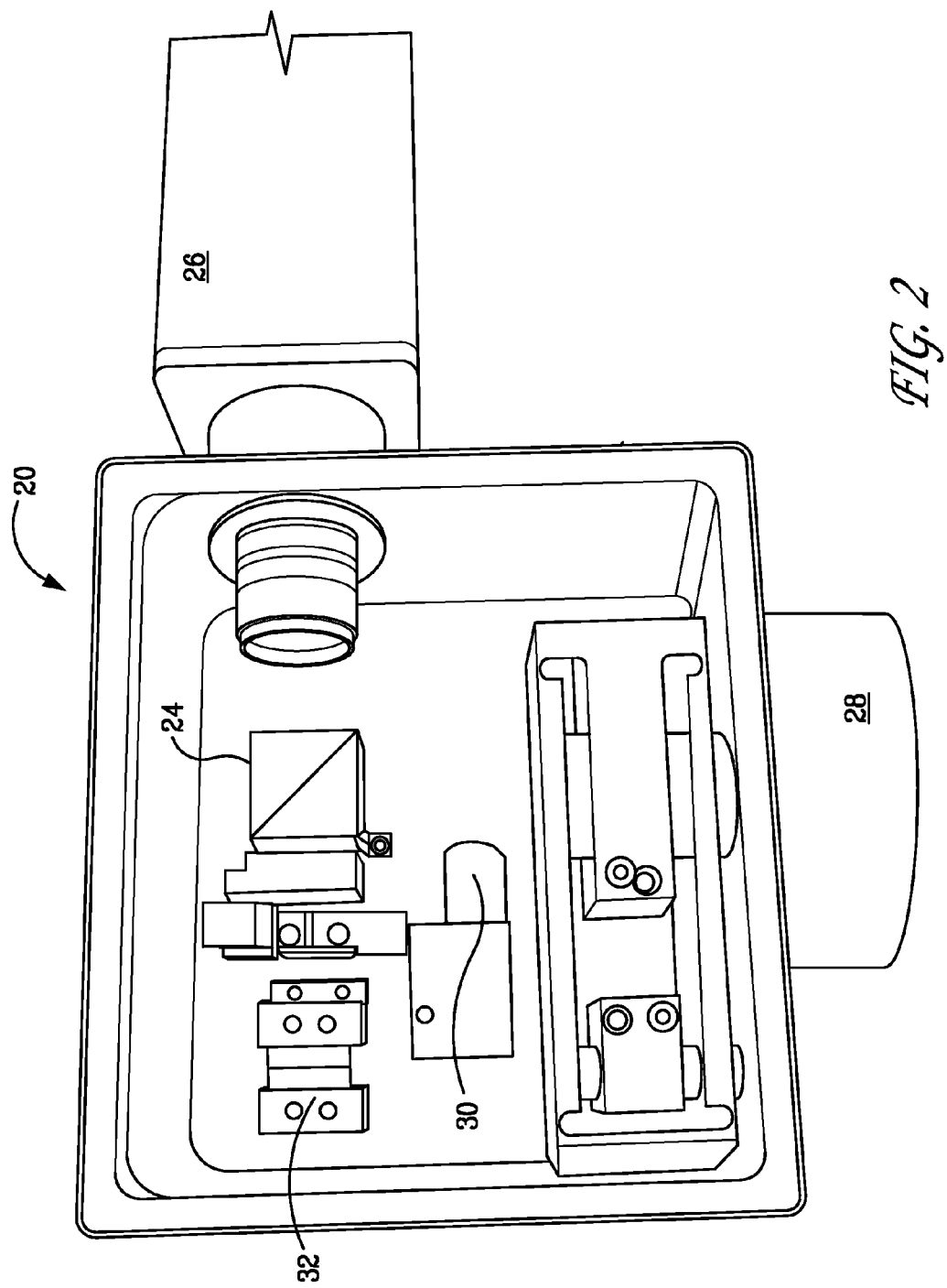
FIG. 2 presents a detailed view of a head unit for use in a system for grading an agricultural product employing hyper-spectral imaging and analysis, in accordance herewith.

A head unit 20 is provided and shown in FIG. 2, with cover panel 22 removed. Prism array 24 is provided for dispersing electromagnetic radiation emitted from an agricultural product into a corresponding spectral image. The range of wavelengths emitted by the prism array can be any range that is broad enough to allow analysis of the agricultural product. In one form, the prism array emits dispersed light having wavelengths in the range of 100 to 2,000 nanometers, or 200 to 1,800 nanometers, or 300 to 1,700 nanometers. In another form the prism array is capable of emitting dispersed light having wavelengths in the range of 300 to 1,600 nanometers. The prism array may have a spectral dispersion of at least 50 nanometers per millimeter (nm/mm), or 100, 125 or 150 nm/mm. The prism array may have at least 100 nm spectral resolution, more preferably 50 nm, or 40, 30, or 20 nm spectral resolution. In one form, the prism array may have a 300 to 1,600 nm spectral range, a spectral dispersion of at least 150 nm/mm and at least a 20 nm spectral resolution.

A light measuring device 26 for detecting component wavelengths within the corresponding spectral image is also provided. In one form, light measuring device 26 may be a high-speed, charge-coupled device (CCD) camera, capable of handling the full range of wavelengths. The CCD camera should be selected to provide high signal to noise ratios with high source light energy at small camera integration time. A suitable CCD camera is available from Hamamatsu Corporation of Bridgewater, N.J.

Still referring to FIG. 2, a lens 28 is provided for directing light emitted from agricultural product P to prism array 24. Reference lasers 30 may be optionally provided for calibration purposes. A micro drive unit 32 may be provided within head unit 20 to enable head unit 20 to be moveably positionable along agricultural product P.

In another form, an interferometer (not shown) may replace prism array 24 within head unit 20. As is well known to those skilled in the art, interferometry makes use of the principle of superposition to combine separate waves together in a way that will cause the result of their combination to have a meaningful property that is diagnostic of the original state of the waves. In operation a single incoming beam of light may be split into two identical beams by a grating or a partial mirror. Each of these beams will travel a different route, called a path, before they are recombined at a detector. The difference in the distance traveled by each beam, creates a phase difference between them. It is this introduced phase difference that creates the interference pattern between the initially identical waves. If a single beam has been split along two paths then the phase difference is diagnostic of anything that changes the phase along the paths. A suitable interferometer and interferometer-based hyper-spectral imaging system is disclosed in U.S. Pat. No. 7,411,682, the contents of which are hereby incorporated by reference in their entirety.

Referring again to FIG. 1, a computer 34 having a processor capable of rapidly handling system data is provided and programmed to compare the detected component wavelengths to a database of previously graded agricultural products to identify and select a grade for the agricultural product P. Computer 34 may be a personal computer having an Intel® Core™2 Quad or better processor. Computer 34 may also interface with head unit controller 36 for controlling the operation of the system 10 and the positioning of the head unit 20 about agricultural product P. A device 38 for providing an uninterrupted source of power to computer 34 may be provided, such devices readily available from a variety of commercial sources.

Figure 3:
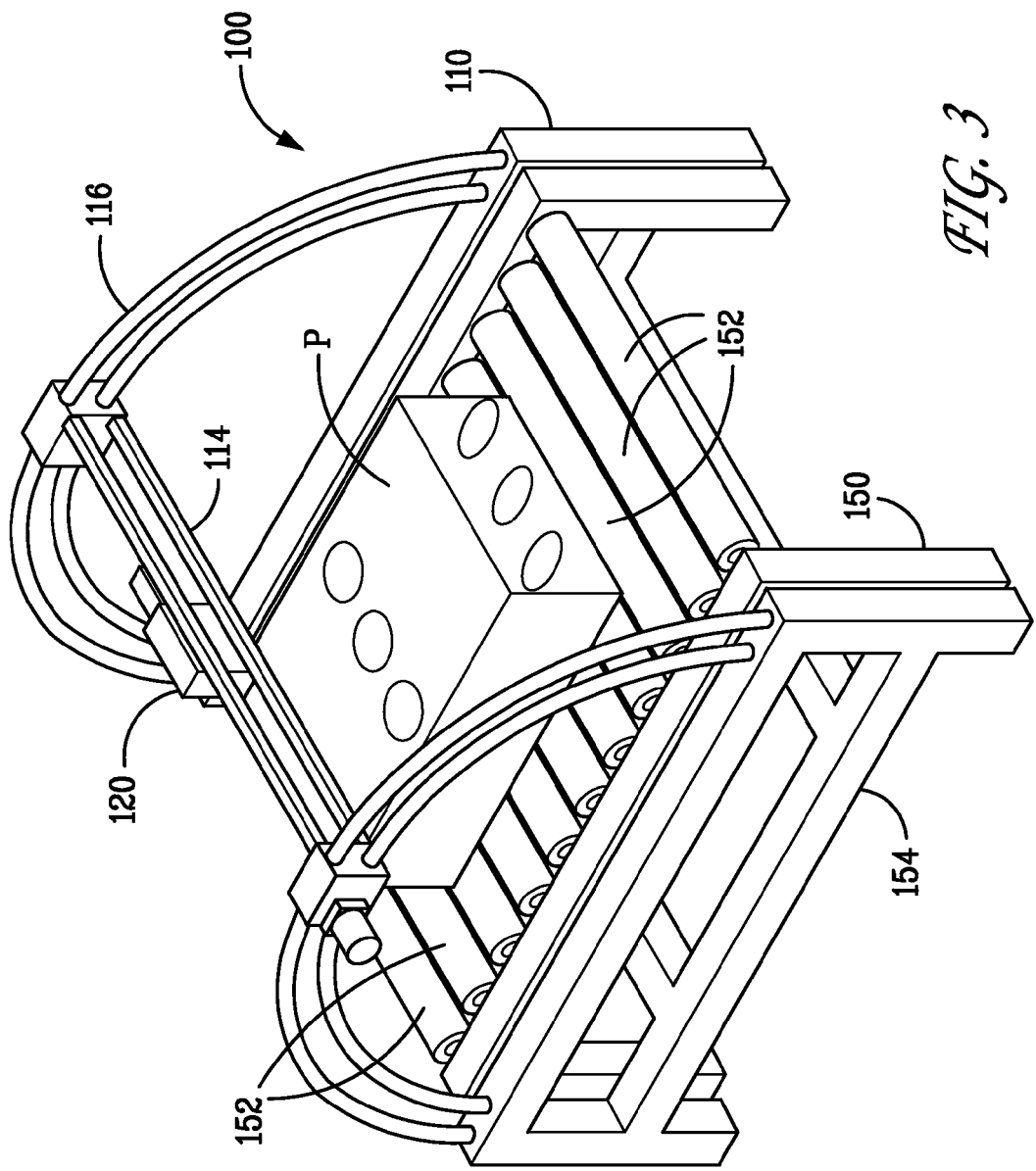
FIG. 3 presents a component of a system for grading an agricultural product having a moveable arm to gather images from a plurality of regions of interest, in accordance herewith.

Referring now to FIG. 3, another form of system 100 for grading an agricultural product P employing hyper-spectral imaging and analysis is shown. The system 10 includes apparatus 110 having at least one light source (not shown) for providing a beam of light. The at least one light source may be mounted on a moveable arm 114 for positioning the at least one light source in proximity to the agricultural product P, when positioned on platform 150. Moveable arm 114 is slideably mounted to frame 116 so that it may traverse along frame 116 and gather images from a plurality of regions of interest of agricultural product P. Frame 116 may be mounted to stand 154 to provide a rigid structure. To facilitate the movement of large bales of agricultural product P, such as tobacco bales, a roller-style conveyer platform 150, having a plurality of rollers 152, may be provided.

Means for movably positioning the moveable arm 114 may be provided to facilitate the scanning of a plurality of regions of interest along the agricultural product P, such means including a servo motor and motor controller. A second light source (not shown) may also be provided and mounted to arm 14.

Figure 4:
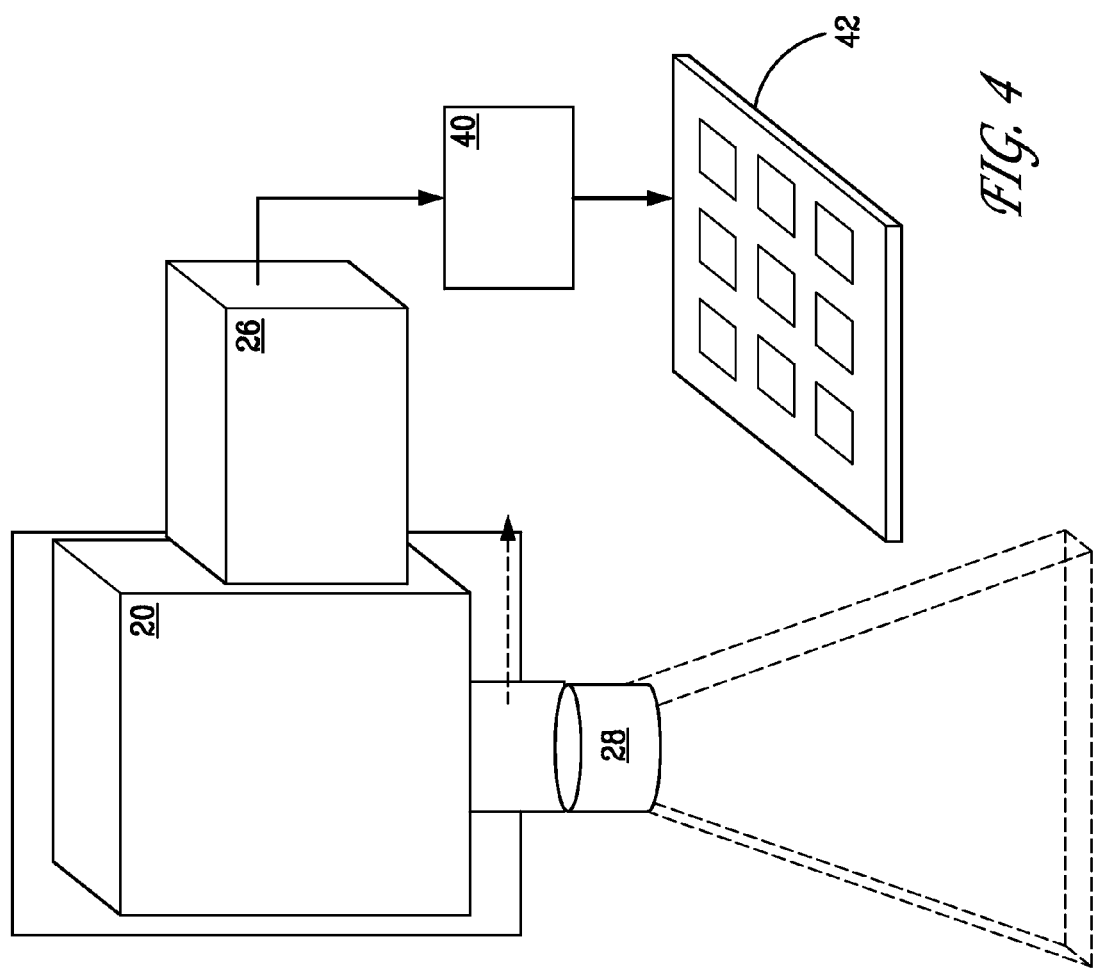
FIG. 4 presents a form of a system for grading an agricultural product that enables the collection of several images, in accordance herewith.

Referring now to FIG. 4, in one form, to enable the collection of several images and provide sufficient representative information regarding agricultural product P, a frame grabber 40 may be employed to produce an array of images 42. As may be appreciated by those skilled in the art, a frame grabber is an electronic device that captures individual, digital still frames from an analog video signal or a digital video stream. Suitable frame grabbers are available from several sources, one such source being DIPIX Technologies Inc. of Ottawa, Ontario, Canada. In one form, frame grabber 40 is a DIPIX Power Grabber™ imaging board employing a high-speed digital signal processor (DSP).

Figure 5:
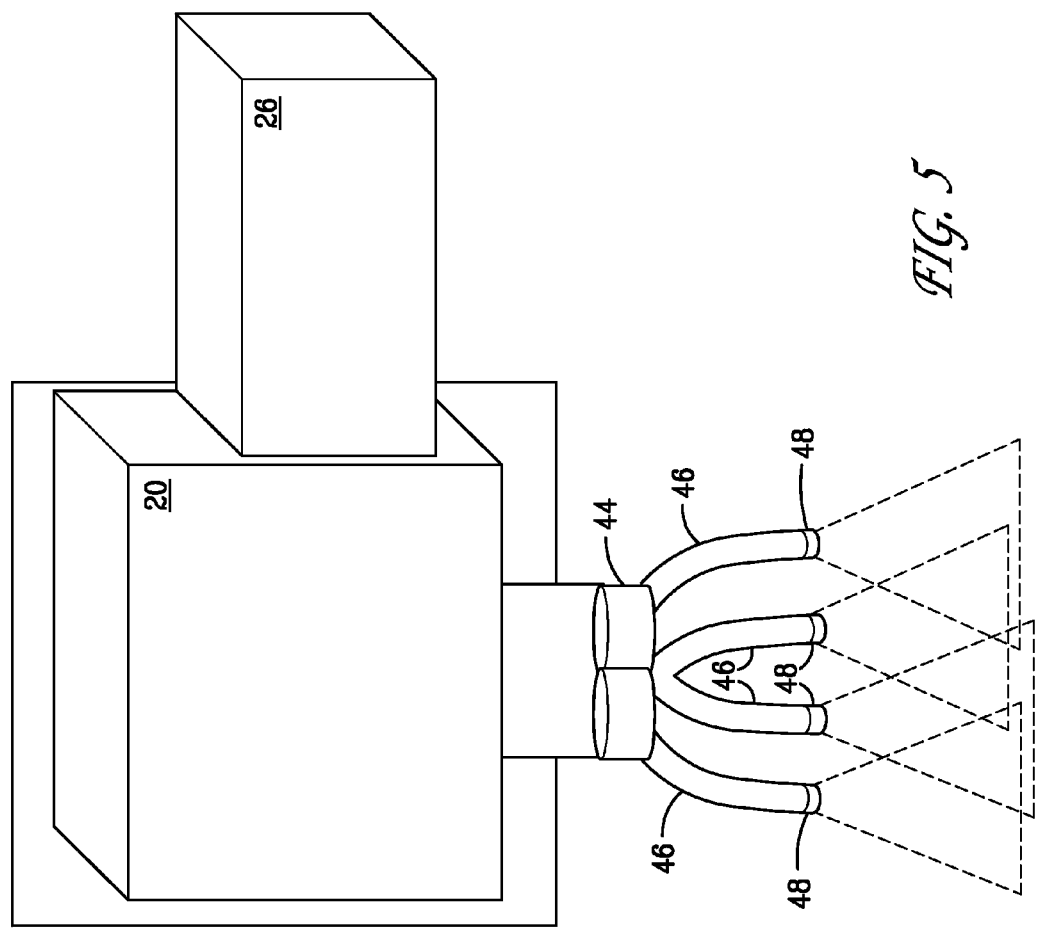
FIG. 5 presents a form of a system for grading an agricultural product that permits multiple fields of view, in accordance herewith.

Referring now to FIG. 5, in another form, to provide sufficient representative information regarding agricultural product P for the imaging spectral analysis, an apparatus for providing multiple fields of view may be provided. The apparatus includes means for sampling electromagnetic radiation emitted from an agricultural product 44 to provide multiple fields of view to the hyper-spectral imaging and analysis system 10. In one form, means for sampling electromagnetic radiation emitted from an agricultural product 44 includes a plurality of fiber optic cables 46, each equipped with an individual fish-eye style lens 46 or, in an alternative form, several small scale CCD cameras (not shown). The use of fish-eye style lens 46 advantageously provides a larger field of view in the development of reflection hyper spectral signatures. In another form, means for sampling electromagnetic radiation emitted from an agricultural product 44 includes an optical splitter (not shown), in place of the plurality of fiber optic cables 46. Suitable fiber optic splitters are available from Microwave Photonic Systems, Inc. of West Chester, Pa. Suitable optical splitters may be obtained from Corning Cable Systems LLC of Hickory, N.C.

Also provided is a method for the automatic on-line grading of an agricultural product, such as a bale of tobacco, via hyper-spectral imaging and analysis. In one form, the method includes the steps of scanning a plurality of regions of interest along the agricultural product, generating hyper-spectral images from the scanned regions of interest, forming a spectral fingerprint for the agricultural product from the hyper-spectral images, comparing the spectral fingerprint to tobacco grade pattern data of a previously graded agricultural product and determining a product grade for the agricultural product. The method disclosed herein has utility in the continuous, virtually real-time measurements of agricultural products, including tobacco.

In one form, the method also includes the steps of determining a physicochemical code for the agricultural product and comparing the physicochemical code to physicochemical code data of previously graded agricultural product.

In another form, the method includes the step of providing multiple fields of view within each region of interest by splitting electromagnetic radiation emitted from an agricultural product. In one form, the step of providing multiple fields of view employs an optical splitter. In another form, the step of providing multiple fields of view employs a fiber optic splitter.

In one form, a learning procedure is performed during which the spectral signature of the materials of interest is learned. Upon learning the spectral signature of an agricultural product, such as tobacco leaf, it may be used for grade identification. As such, the system disclosed herein is first exposed, at the learning phase, to reflection from various grades in order for it to recognize the grade being analyzed.

Advantageously, the method and system disclosed herein provides a chemical imaging platform that enables speed and exceptionally high sensitivity, thus accurate and non-destructive nature, wherein measurement time is greatly reduced. This enables the tracking of the monitored material with high repeatability.

The method and system disclosed herein provides a highly sensitive hyper spectral imaging analyzer with co-sharing database capabilities. The digitized highly sensitive imaging system disclosed herein enables the imaging of materials components, more detailed observation and provides more specific, sensitive, accurate and repeatable measurements. This may be achieved using advanced image recognition technologies, as well as adaptive and collaborative data bases and statistical and spectral algorithms.

The method and system disclosed herein is capable of characterizing the composition of inorganic, organic, and chemical particulate matter suspended in tobacco. The instrument scans leaf samples, analyses the scanned samples' wavelength signature, performing trends analysis and compares the gathered data to data bases that may, in one form, be continuously updated. The system then generates reports for system users. A remote network may be provided to support the gathering of data for integrated database construction as well as to support remote professional personnel in real time.

Advantageously, the proposed method requires no sample preparation. In operation, linear calibration plots in the ppm range are obtained for mono-component contamination and for simple compound mixtures in this matrix. Non-contact, non-destructive, near real time on-line, automated physicochemical imaging, classification and analysis of a sample of tobacco leafs is provided without the need for consumable materials for sample processing. The system operates using algorithms and software packages, together with unique ultra-high resolution optical components and a two-dimensional sample positioning of regions of interest for generating, for example, five dimensional (5D) spectral images of the tobacco sample under analysis.

Figure 6:
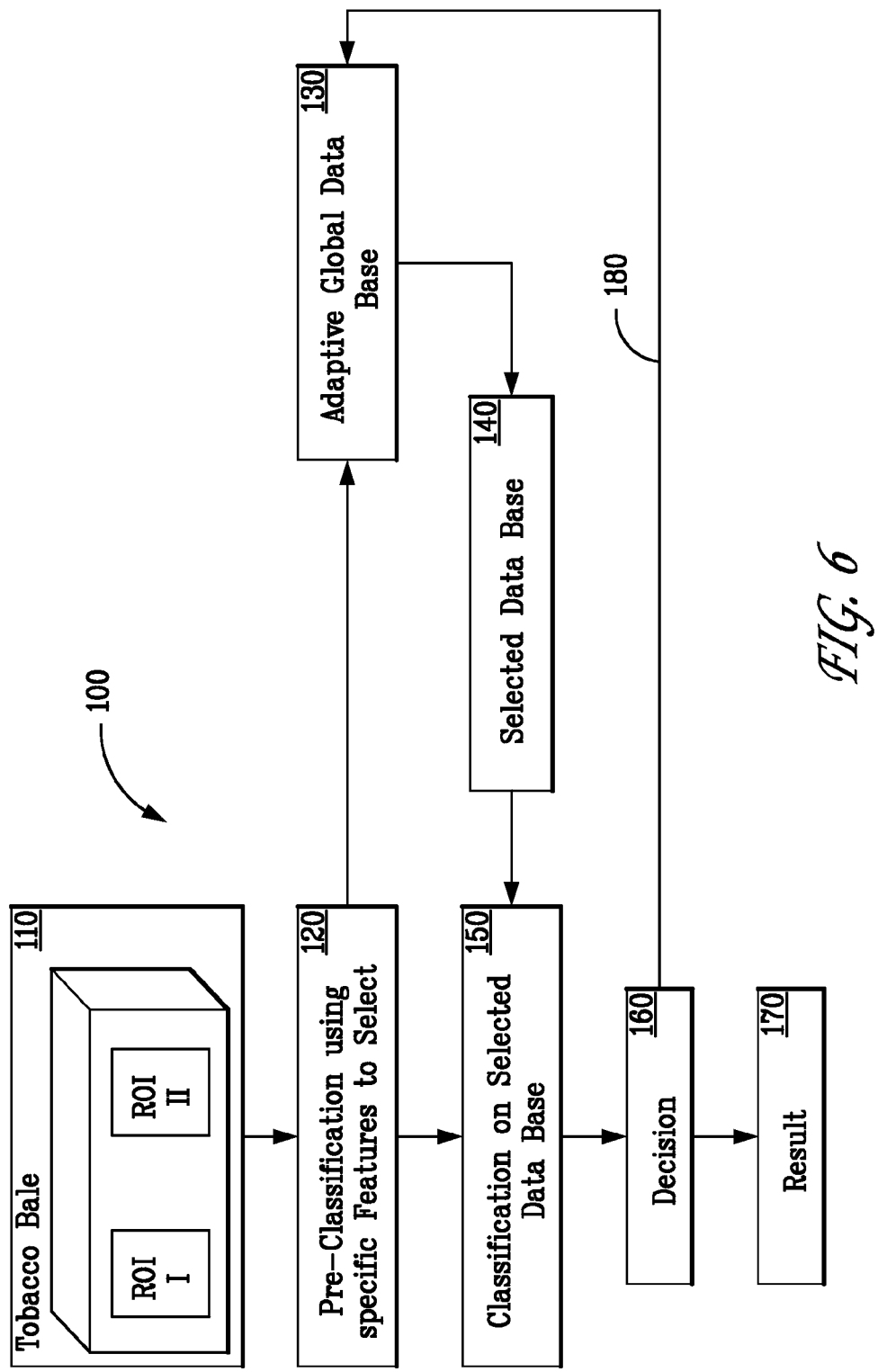
FIG. 6 presents a method for grading an agricultural product via hyper-spectral imaging and analysis, in block diagram form, in accordance herewith.

Referring now to FIG. 6, in operation, method 100 may include the following steps: scanning at least one or a plurality of regions of interest (ROI) and generating hyper spectral images 110; a pre-classification step 120 to initially select a database from among a plurality of databases; a classification step 150, which uses a physicochemical mechanism employing grading logics and spectral/energy band data to arrive at, in the case of tobacco, a tobacco grade pattern (TGP); a decision and identification of grade step 160; a database updating step 180, wherein the database is updated by the inclusion of data relating to the just-graded sample; and a reporting step 170.

Pre-classification step 120 may utilize information such as region of origin of the bale (location) and harvesting season (time of year), together with the hyper spectral images generated in step 110 to initially select from among several databases stored within adaptive global database 130, a selected database 140 for use in classification grading step 150. As may be appreciated by those skilled in the art of tobacco grading, a plurality of databases are required to account for seasonal, regional and weather variations over time and for the various tobacco types that may be graded. Using location as an example (e.g., Georgia, South Carolina, Eastern Carolina, Old Belt) enables the pre-selection of a partial database of book marks and floor marks to enhance the system's classification performance.

Test results are based on the scanning and counting of individual samples, each comprising dozens of scans, and each sample classified using spectral band features, spectral finger prints (SFP), major spectral representative components, purity and quality of each major compound (component, SFP), relative quantity of each SFP and, optionally, crystallization and morphological features.

Figure 7:
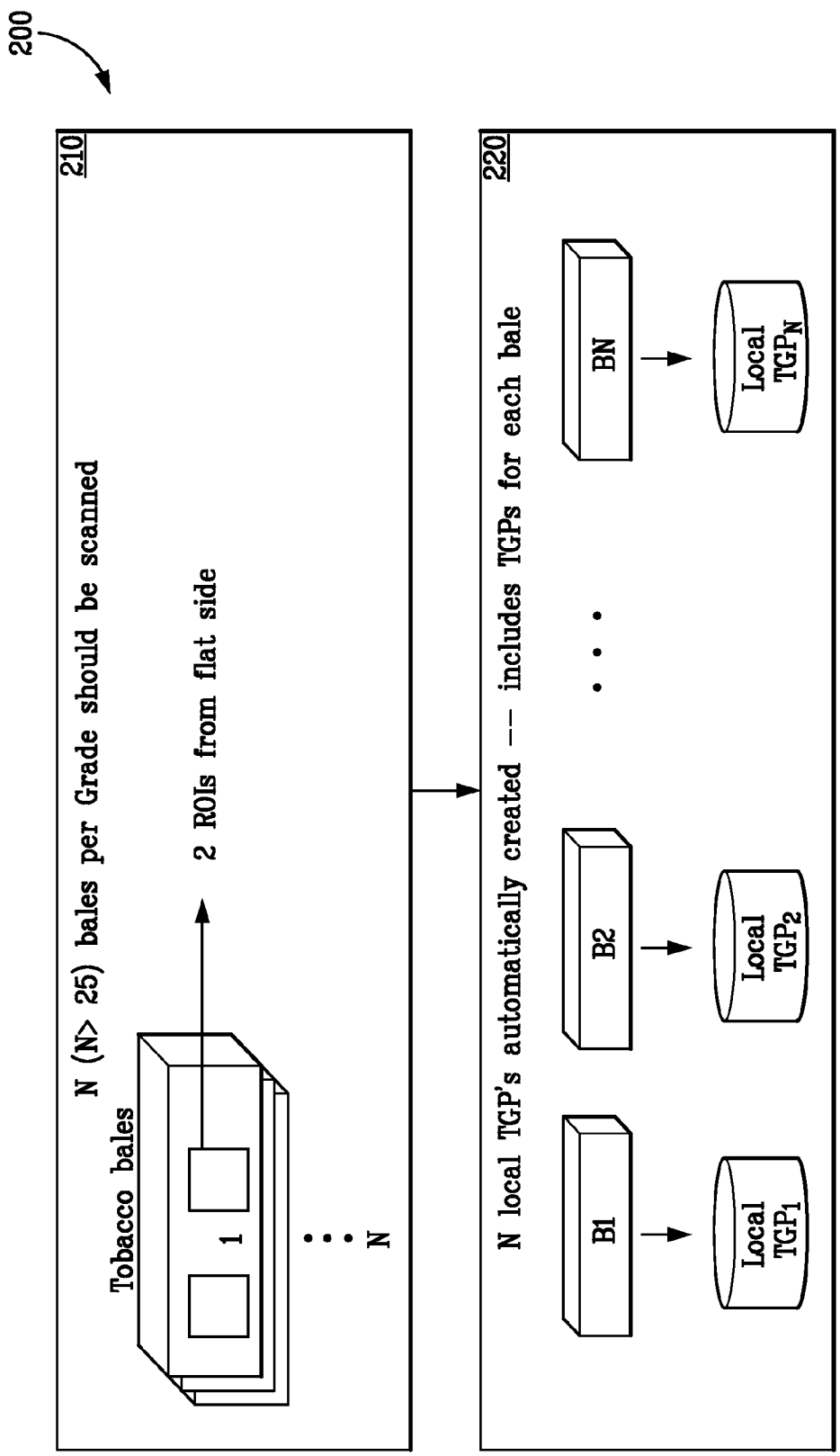
FIG. 7 presents a block diagram of a learning phase for use in a method for grading an agricultural product via hyper-spectral imaging and analysis, in accordance herewith.

Referring now to FIG. 7, one form of a learning phase 200 will be described. A plurality of samples bales of graded agricultural products, such as tobacco bales are scanned in step 210. As indicated, for tobacco bales, a significant number of bales should be scanned in order that the impact of bale variability is reduced. In practice, it has been observed that the impact of bale variability can be reduced when the number of bales N is at least about 25 per grade. For each different tobacco grade, hyperspectral images are collected for each bale to create a grade-related database. Tobacco bales may be scanned using xenon and/or mercury light sources for grading and an optional ultraviolet light source may be used for chemical signature classification, which can assist in improving the grading of floor marks also.

In operation, the light source(s) is activated (one, two, three or more spot lights in parallel to the region of interest (ROI)), permitting redundant data to be gathered. A plurality of regions of interest (such as by way of example, but not of limitation, a 20 cm×20 cm area for each ROI) is scanned for each grade and bale to provide two or three hyperspectral images. Scanning is performed and the reflection spectral grading signature and optional fluorescence spectral chemical signature received. The images are then saved. As depicted in step 220, N local tobacco grade patterns (TGP) are created, each corresponding to the physicochemical codes obtained for each bale. A database for each grade (including bookmarks and optionally floor marks) is thus formed from the combined information obtained for the N bales and master grader information. The database so produced may be refined using information regarding tobacco graded incorrectly, identified as a different grade (false positive); optional detection of sub-grading and a validation of classification repeatability may be generated. In one form, optional checking of new spectral fingerprints of grades is employed to ensure database stability.

As such, provided herein is a method of developing a tobacco grading database for use with a system for grading tobacco employing hyper-spectral imaging and analysis, the method comprising the steps of (a) passing at least one light source along a tobacco bale, the tobacco bale previously graded by a human grader; (b) generating a plurality of hyper-spectral images by sampling electromagnetic radiation emitted from the tobacco bale; (c) forming a tobacco grade pattern for the tobacco bale from the hyper-spectral images; (d) storing the tobacco grade pattern within a computer storage means; (e) repeating steps (a)-(d) a plurality of times using a plurality of tobacco bales, each tobacco bale previously graded by a human grader and receiving a substantially identical grade; and (f) forming an overall tobacco grade pattern that corresponds to the grade provided by the human grader.

Figure 8:
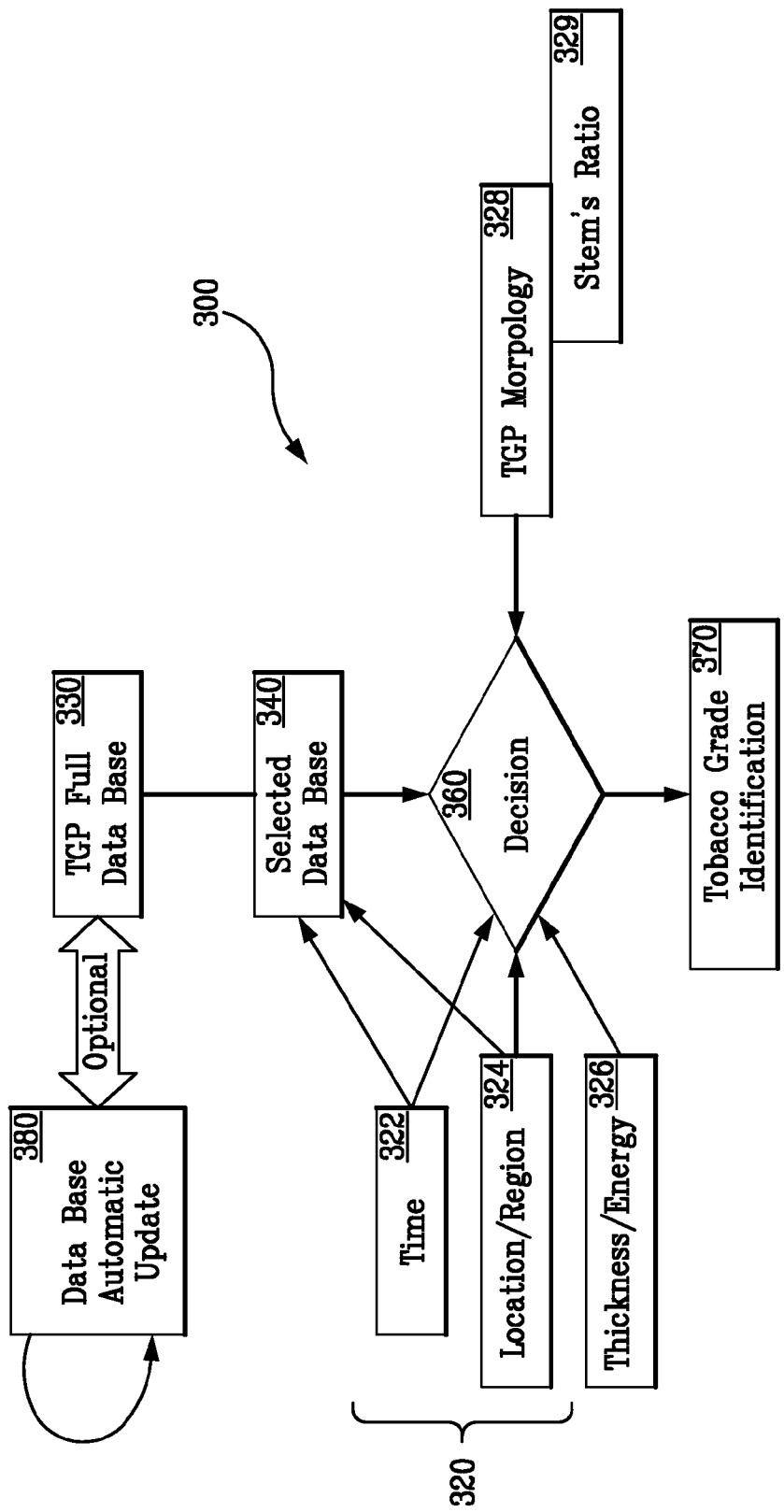
FIG. 8 presents a block diagram of an adaptive system algorithm for use in a method for grading an agricultural product via hyper-spectral imaging and analysis, in accordance herewith.

Referring now to FIG. 8, one form of an adaptive system algorithm 300 is shown. The algorithm 300 includes a pre-classification step 320 using information such as location/region of origin of the bale 324 and time of year (harvesting season) 322. A plurality of databases 330 (full database) are provide to account for seasonal, regional and weather variations over time and for the various tobacco types that may be graded. Pre-classification step 320 is used to select among them and obtain selected database 340. Information obtained from scanning and hyper-spectral imaging and analysis, including thickness/energy 326, TGP morphology 328 and stem ratio 329 are used in the grading decision process 360 to identify the grade in step 370. The full database 330 may optionally be updated by the inclusion of data relating to the just-graded sample 380.

During scanning, a picture or frame is formed by the CCD camera from the spectra dispersed by the prism array or the mirrors of an interferometer. The picture or frame includes an array of pixels, which may be, by way of example, but not of limitation, on the order of about a 480 pixel by 400 pixel array. Such a picture or frame would thus contain about 192,000 pixels. As may be appreciated by those skilled in the art, each pixel may contain about 500 spectra for an agricultural product such as tobacco. The database for each tobacco grade is in the form of a tobacco grade pattern (TGP) of spectral finger prints and physicochemical codes. The TGP provides a fingerprint which is compared to the information contained in the scanned array of pixels for the particular bale or container of agricultural product. A result or grade may thus be obtained with a measure of confidence associated therewith.

Figure 9:
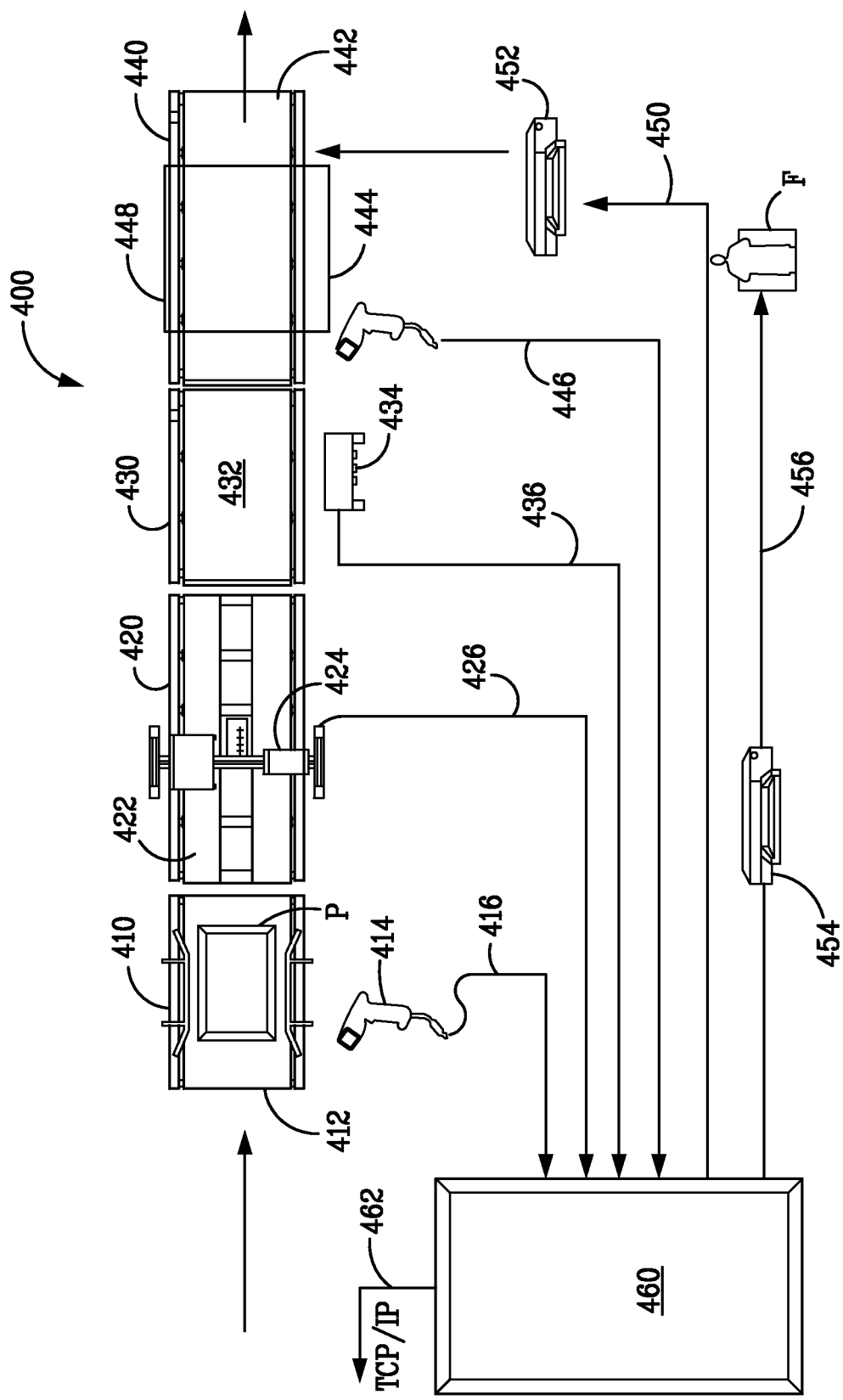
FIG. 9 presents a schematic view of an automatic grading system, in accordance herewith.

Referring now to FIG. 9, a system 400 for the automatic grading of an agricultural product, such as a tobacco bale P, is shown. As shown, system 400 includes a loading station 410, having a conveyer 412, wherein, in one form, a bar code reader 414 logs basic information regarding the tobacco bale P, such as farmer, farm, location, date, etc., and sends the information electronically over line 416 to computer 460. As may be appreciated, bale P can include a "buy coupon" having a unique identifier for uniquely identifying each bale P. Tobacco bale P may next move on to moisture and, optionally, density measurement station 420 via conveyor 422, wherein moisture sensor and, optionally, density sensor 424 determines moisture and density measurements and sends the information electronically over line 426 to computer 460. A suitable moisture and density measurement station may be obtained from MALCAM Inc. of Short Hills, N.J., one example being a MALCAM Model No. MMA-4020.

Still referring to FIG. 9, tobacco bale P may next move on to weighing station 430 via conveyor 432, wherein sensor 434 determines bale weight and sends the information electronically over line 436 to computer 460. A suitable weighing station may be obtained from a variety of sources.

Tobacco bale P may next move on to a system 440 for grading an agricultural product employing hyper-spectral imaging and analysis, of the type disclosed herein. Tobacco bale P may move along conveyer 442 until positioned in proximity with at least one light source for providing a beam of light, which may be located within an enclosure or chamber 448 so as to provide a darkened zone for better system performance. As described herein above, system 440 also includes a prism array (not shown) for dispersing light reflected from the plurality of light beams into a corresponding spectral image, a light measuring light device (not shown) for detecting component wavelengths within the corresponding spectral image and a processor (not shown) operable to compare the detected component wavelengths to a database of previously graded agricultural products to identify and select a grade for the agricultural product. An optional bar code reader 446 may be positioned at this point to log additional information. As may be appreciated, the processor may be a stand-alone device or computer 460, programmed to provide this functionality.

The information can be processed by computer 460 and displayed in real-time for the operator or sent via line 462 over the internet to a remote location or uplinked to a satellite. As may be appreciated, information may be relayed via line 462, by way of example, but not of limitation, to a financial office of the purchaser of the agricultural product P, whereby transactional information may be recorded, relayed for business and product planning purposes. In one form, the financial office can send authorization over line 462, to computer 460, which may send a command to issue a check over line 456 to printer 454, which may then print a check on-site to the farmer F. Such information can also be processed via other means, or transferred over phone line connections, local area network (LAN) connections, and/or stored via tape backup, CD ROM, and the like, as will be appreciated by those skilled in the relevant art(s).

While FIG. 9 has been described for the case where the agricultural product P is a tobacco bale, application to other forms of agricultural products are envisioned, including seeds.

All or a portion of the devices and subsystems of the exemplary forms can be conveniently implemented using one or more general purpose computer systems, microprocessors, digital signal processors, micro-controllers, and the like, programmed according to the teachings of the exemplary forms disclosed herein, as will be appreciated by those skilled in the computer and software arts.

In view thereof, in one form there is provided a computer program product for facilitating tobacco grading, including one or more computer readable instructions embedded on a tangible computer readable medium and configured to cause one or more computer processors to perform the steps of determining bale weight, tobacco leaf grade and, optionally, moisture content and transmitting information relating to the optionally determined moisture content, bale weight, and tobacco leaf grade over a communications link.

Appropriate software can be readily prepared by programmers of ordinary skill based on the teachings of the exemplary forms, as will be appreciated by those skilled in the software art. Further, the devices and subsystems of the exemplary forms can be implemented on the World Wide Web. In addition, the devices and subsystems of the exemplary forms can be implemented by the preparation of application-specific integrated circuits or by interconnecting an appropriate network of conventional component circuits, as will be appreciated by those skilled in the electrical art(s). Thus, the exemplary forms are not limited to any specific combination of hardware circuitry and/or software.

Stored on any one or on a combination of computer readable media, the exemplary forms disclosed herein can include software for controlling the devices and subsystems of the exemplary forms, for driving the devices and subsystems of the exemplary forms, for enabling the devices and subsystems of the exemplary forms to interact with a human user, and the like. Such software can include, but is not limited to, device drivers, firmware, operating systems, development tools, applications software, and the like. Such computer readable media further can include the computer program product of a form disclosed herein for performing all or a portion (if processing is distributed) of the processing performed in implementing the methods disclosed herein. Computer code devices of the exemplary forms disclosed herein can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the exemplary forms disclosed herein can be distributed for better performance, reliability, cost, and the like.

As stated above, the devices and subsystems of the exemplary forms can include computer readable medium or memories for holding instructions programmed according to the forms disclosed herein and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

The forms disclosed herein, as illustratively described and exemplified hereinabove, have several beneficial and advantageous aspects, characteristics, and features. The forms disclosed herein successfully address and overcome shortcomings and limitations, and widen the scope, of currently known teachings with respect to the grading of tobacco bales.

The forms disclosed herein, provide for grading methodologies (protocols, procedures, equipment) of tobacco bales, which are highly accurate and highly precise (reproducible, robust), during tobacco bale final selection processes. The forms disclosed herein, provide high sensitivity, high resolution, and high speed (fast, at short time scales), during automatic operation, in an optimum and highly efficient (cost effective) commercially applicable manner.

As may be appreciated, the performance of the methods and systems disclosed herein is dependent upon the number of regions scanned, image sizes, light sources, filters, light source energy stability, etc.

It is to be fully understood that certain aspects, characteristics, and features, of the forms disclosed herein, which are illustratively described and presented in the context or format of a plurality of separate forms, may also be illustratively described and presented in any suitable combination or sub-combination in the context or format of a single form. Conversely, various aspects, characteristics, and features, of the forms disclosed herein, which are illustratively described and presented in combination or sub-combination in the context or format of a single form, may also be illustratively described and presented in the context or format of a plurality of separate forms.

All patents, patent applications, and publications, cited or referred to in this specification are herein incorporated in their entirety by reference into the specification, to the same extent as if each individual patent, patent application, or publication, was specifically and individually indicated to be incorporated herein by reference. In addition, citation or identification of any reference in this specification shall not be construed or understood as an admission that such reference represents or corresponds to prior art. To the extent that section headings are used, they should not be construed as necessarily limiting.

While the forms disclosed herein have been described in connection with a number of exemplary forms, and implementations, the forms disclosed herein are not so limited, but rather cover various modifications, and equivalent arrangements, which fall within the purview of the present claims.

What is claimed:

1. A method of developing an agricultural product grading database for use with a system for grading agricultural product employing hyper-spectral imaging and analysis, the method comprising the steps of:
   (a) passing at least one light source along the agricultural product, the agricultural product previously graded by a human grader;
   (b) generating a plurality of hyper-spectral images by sampling electromagnetic radiation emitted from the agricultural product;
   (c) forming an agricultural product grade pattern for the agricultural product from the hyper-spectral images;
   (d) storing the agricultural product grade pattern within a computer storage means;
   (e) repeating steps (a)-(d) a plurality of times using a plurality of agricultural products, each agricultural product previously graded by a human grader and receiving a substantially identical grade;
   (f) forming an overall agricultural product grade pattern that corresponds to the grade provided by the human grader;
   (g) providing a plurality of databases to account for seasonal, regional and weather variations over time and for the various agricultural product types graded by the human grader; and
   (h) updating the plurality of databases to include data relating to the agricultural product.

2. The method of claim 1, wherein the number of times step (e) is performed is selected to reduce the impact of variability on the overall agricultural product grade pattern.

3. The method of claim 1, wherein said at least one light source for providing a beam of light comprises a xenon light source.

4. The method of claim 1, wherein said at least one light source for providing a beam of light comprises a mercury light source.

5. The method of claim 1, wherein said at least one light source for providing a beam of light comprises a laser diode.

6. The method of claim 1, wherein said at least one light source for providing a beam of light comprises an ultraviolet light source.

7. The method of claim 6, wherein said at least one light source for providing a beam of light further comprises a mercury light source and a xenon light source.

* * * * *